United States Patent [19]

Hackett et al.

[11] Patent Number: 5,158,893
[45] Date of Patent: Oct. 27, 1992

[54] METHODS AND COMPOSITIONS FOR SCREENING CARCINOMAS

[75] Inventors: Adeline J. Hackett; Shahnaz H. Dairkee, both of Orinda, Calif.

[73] Assignee: Peralta Cancer Research Institute, San Leandro, Calif.

[21] Appl. No.: 511,806

[22] Filed: Apr. 17, 1990

Related U.S. Application Data

[63] Continuation of Ser. No. 298,276, Jan. 13, 1989, abandoned, which is a continuation of Ser. No. 940,702, Dec. 11, 1986, abandoned.

[51] Int. Cl.$^5$ .............. C07K 15/28; G01N 33/574; G01N 33/577
[52] U.S. Cl. .................. 435/721; 435/7.23; 435/960; 436/63; 436/64; 436/548; 436/813; 530/808; 530/388.85; 530/388.2; 935/110
[58] Field of Search ............ 436/501, 503, 528, 548, 436/63, 64, 813; 530/357, 387, 808; 424/85; 514/2; 435/172.2, 7.23, 960, 975, 7.21, 240.27; 935/110

[56] References Cited

U.S. PATENT DOCUMENTS 4,340,535  7/1982  Voisin et al. .................. 424/85
4,599,304  7/1986  Lanier et al. .................. 424/85
4,612,282  9/1986  Schlom et al. ................ 436/548

OTHER PUBLICATIONS

Barry A. Gusterson, et al., "Identification of Myoepithelial Cells in Human and Rat Breasts by Anti-Common Acute Lymphoblastic Leukemia Antigen Antibody A12," JNCI, Aug. 1986.

Peter J. Dempsey, et al., "A Monoclonal Antibody ClBr17 Recognizes a Myoepithelium-Specific Antigen in Human Mammary Gland," Int. J. Cancer, 1986.

Monoclonal antikeratin antibody: production, characterization, and immunohistochemical application, Eto et al., *Chem Abst* 102:202277f (1985).

*Primary Examiner*—David Saunders
*Attorney, Agent, or Firm*—Townsend & Townsend

[57] ABSTRACT

Methods for determining the prognosis of human carcinomas utilizing a marker specific for malignant cells of aggressive cancers. Cell lines have been produced that secrete monoclonal antibodies useful in detecting such markers, including a 51,000-dalton keratin protein, specific for myoepithelial cells, e.g., in tissue culture. Pharmaceutical compositions containing these antibodies, which can be in combination with cytotoxic agents and the use of such compositions in the management of carcinomas are included.

Prior to filing of this patent application, the continuous transformed cell lines described herein was deposited in the American Type Culture Collection and designated Accession No. HB9288.

8 Claims, 1 Drawing Sheet

FIG. 1A.
FIG. 1B.
FIG. 2A.
FIG. 2B.
FIG. 2C.
FIG. 3A.
FIG. 3B.

METHODS AND COMPOSITIONS FOR SCREENING CARCINOMAS

This is a continuation of application Ser. No. 298,276, filed Jan. 13, 1989, now abandoned, which is a continuation of application Ser. No. 06/940,702, filed Dec. 11, 1986, now abandoned.

FIELD OF THE INVENTION

The present invention relates generally to the analysis of normal and cancerous epithelial tissue, and more specifically, to means for detecting the existence of particularly aggressive neoplasms for prognosis.

BACKGROUND OF THE INVENTION

Human mammary epithelium is located within a network of branched ducts terminating in lobules, is surrounded by a basement membrane, and is embedded in fat and connective tissue. The epithelium of the mammary gland has been classically subdivided into two categories, i.e., luminal cells that border the lumen and basal cells also referred to as myoepithelial cells that are situated between the basement membrane and the luminal epithelium.

Myoepithelial cells are derived from ectoderm and are known to exhibit both epithelial and mesenchymal characteristics (Cutler and Chaundry (1973) *J. Morphol.*, 140:343–354, and Franke et al. (1980) *J. Cell, Biol.*, 84:633–654, both of which are incorporated herein by reference). They are situated between acinar or ductal luminal cells and the basal lamina in a number of secretory glands, such as breast, lacrimal, eccrine, and apocrine sweat glands and various salivary glands.

A major problem in studies of human mammary-gland differentiation both in vivo and in culture has been the lack of markers which allow a rapid, reproducible, and clear definition of the two epithelial subclasses. Similarly, a major problem in the accurate diagnosis of the malignancy of mammary and other epithelial neoplasms stems in part from this same lack of suitable markers.

For some tumors, marker typing often provides oncologists with crucial prognostic insights, which in turn dictates the most suitable treatment regimen. For example, while a nonagressive tumor may be surgically removed without significant risk of recurrence or metastasis, the removal of an aggressive tumor must be generally accompanied by the induction of drugs, isotopes or other chemotherapeutic agents to ensure cure. In addition to the expense of such aggressive treatments, the patient can experience very severe side-effects.

Although considerable advances have been made recently in the typing of some carcinomas (such as by immunocytochemical procedures), the severity of most remains uncertain until the disease has progressed. This is particularly true of mammary carcinomas, where even the commonly utilized estrogen and progesterone receptor assays cannot predict tumor invasiveness, recurrence or other aggressive characteristics.

Accordingly, there exists a significant need for a reliable marker based analysis useful in the prognosis of human mammary and other carcinomas, as well as in the characterization of subclasses of normal epithelial cells in tissue culture. The present invention fulfills these needs.

SUMMARY OF THE INVENTION

The present invention provides a method for determining the prognosis of a malignant carcinoma which comprises detecting marker distribution in a sample of malignant cells from the carcinoma, the markers being basal or myoepithelial cell-specific, and comparing the distribution with known distributions of such markers in aggressive (typically a homogeneous distribution) or non-aggressive cancers. One suitable marker is a human keratin protein of about 51,000 daltons, which typically will be found on a significant portion of malignant cells in the carcinoma in cases of aggressive tumors. This marker is also found to be homogeneously expressed on basal cells in mammary-gland tissue cultures.

Novel cells lines are provided which can produce monoclonal antibodies capable of specifically reacting with the markers. These antibodies are useful in the diagnosis and therapy of various carcinomas, particularly mammary carcinomas, and in investigations of epithelial cell proliferation and differentiation under tissue-culture conditions.

BRIEF DESCRIPTION OF THE FIGURES

FIGS. 1a and 1b are photographs of cryostat sections of mature, normal mammary ducts from two reduction mammoplasty sections showing reactivity with the monoclonal antibody 312C8-1. Arrows indicate a myoepithelial layer at the base of the duct ($\times$400).

FIGS. 2a, 2b, and 2c are photographs of cryostat sections showing monoclonal antibody 312C8-1 reactivity with a salivary gland secretory duct indicating a continuous myoepithelial layer (FIG. 2a): salivary gland acini showing strong staining of the basket-like myoepithelial cells (FIG. 2b): and sweat glands in skin displaying intense reactivity of the myoepithelium (FIG. 2c). Arrows indicate the myoepithelial layer ($\times$400).

FIG. 3 shows the patterns of reactivity of the monoclonal antibody 312C8-1 with two mammary carcinoma specimens. FIG. 3a shows the strong, homogeneous pattern of reactivity with cells from an aggressive tumor (arrow) and FIG. 3b shows a strong, heterogeneous pattern, encircling tumor nests, indicative of a nonaggressive tumor ($\times$180).

DESCRIPTION OF THE SPECIFIC EMBODIMENTS

The present invention provides methods and compositions for the identification and diagnosis of human mammary and other carcinomas, i.e., the presence of myoepithelial or basal cell-specific markers distributed homogeneously throughout samples of carcinomas has been found, very surprisingly, to be highly predictive of an aggressive form of epithelial neoplasm. The compositions are also useful in characterizing epithelial cells in tissue culture.

In accordance with one embodiment of the present invention, novel immortalized cells capable of producing monoclonal antibodies, and compositions comprising such antibodies, are provided. These compositions are capable of selectively binding to a neoplastic cell-specific marker, such as a 51,000-dalton keratin polypeptide exhibiting an isoelectric point of about 5.4. This antigen is expressed naturally in vivo and in vitro, as shown by tissue culture studies, which also indicate that it is epithelial subclass-specific for basal cells.

Based on cytoskeletal extracts, the preferred keratin marker closely corresponds to keratin 14, characteristics of which are detailed in Moll et al. (1982) Cell. 31:11–24, which is incorporated herein by reference. This keratin is present in many organ systems, however, it appears restricted to the basal epithelium of tissues commonly located in the human mammary gland. This 51,000-dalton cytokeratin is likely a differentiation antigen of the basal epithelial cells of the human mammary gland.

By utilizing a monoclonal antibody specific for the 51,000-dalton keratin, it was found that about 4% of breast carcinomas exhibit homogeneous distribution patterns of the protein throughout the surgical sample of malignant cells. These carcinomas are thus likely to be of basal origin. In each instance, these carcinomas were extremely aggressive and were either ultimately fatal or resulted in early recurrent disease postmastectomy. Thus, it was discovered that carcinomas expressing the 312C8-1 marker are virulent and should be treated aggressively.

By a variety of techniques well-known to those in the art, one can screen tumor cells from a sample for the presence of malignant cells bearing that antigen or other markers specific for cells of basal origin in the samples, and grade the severity of malignancy. Typically, the distribution of the markers will be compared with one or more known distributions from varying grades of tumors, e.g., aggressive and non-aggressive. The presence of the marker on a majority of the malignant cells usually indicates the presence of an aggressive cancer. This knowledge can in turn be useful in selecting the ideal mode of therapy.

The carcinomas suitable for testing in accordance with the present invention are generally of glandular tissue origin. By way of example, but not limitation, such tissues include breast, salivary, lachrymal, prostate, thymus and adnexal tissues. Aggressive grades of cancer are those classified presently as the primary cause of a fatality, typically within about two to three years of onset, but in some instances about five years of onset. These cancers are also alternatively classified by a high incidence of recurrence after treatment, typically a recurrence rate (e.g. metastasis) of about 75% to 90% or more.

Although a preferred marker of the present invention is a keratin, those skilled in the art will realize that a variety of markers such as other proteins, glycoproteins, lipoproteins, polysaccharides, and the like, which are produced by the myoepithelial cells forming the carcinoma, can be utilized in accordance with the present invention. Preferably, the marker will be specific for the neoplastic cell with respect to other markers on cells commonly present in the sample to be analyzed (e.g., other tissue from the carcinoma sample, serum, etc.).

Ideally, the markers will be antigenic, at least in a foreign host, to permit the production of reactive antibodies. With antibodies, the presence of the markers may be readily determined immunologically, employing conventional immunoassays or histochemical staining procedures. The monoclonal antibodies may be used intact, or as fragments, such as Fv, Fab, or F(ab')$_2$.

In histochemical assays, the complexes of antibodies and markers from myoepithelial cells will form patterns, which can be compared to patterns of complexes from known aggressive or non-aggressive carcinomas. Typically, a homogeneous pattern of reactivity will be indicative of an aggressive carcinoma. The pattern or members of complexes will vary somewhat from one patient to another, with the particular carcinoma, and with the particular assay system utilized. An exemplary homogeneous pattern is shown in FIG. 3A, wherein a substantial portion of the malignant cells bear the marker, commonly at least about 50%. More commonly, at least 70% to 85%, and most commonly 90% to 95% or more.

The antibodies can be prepared by injecting the desired immunogen into a foreign host, in accordance with conventional techniques. Suitable foreign hosts include mammals, such as mice, rats, sheep, rabbits, etc. The immunogen typically consists of whole or lysed myoepithelial cells, isolated from normal or cancerous patients, or from cells or cell lines grown in tissue culture. The cells, or antigenic preparation thereof, may be injected intramuscularly, intraperitoneally, subcutaneously, or the like, usually in conjunction with an adjuvant to increase antigenicity. Usually, the animals are bled periodically, with successive bleeds exhibiting improved titer and specificity for the antigens of choice.

Alternatively, monoclonal antibodies may be produced for use in the present invention. Typically, monoclonal antibodies are obtained from immortalized cell lines, such as produced by the fusion technique of Koehler and Milstein (1975) Nature, 256:495. The antibody-producing lymphocytes used in the fusions are obtained from a host exposed to the foreign antigen. These cells are fused, typically, between suitable drug-marked human myeloma, mouse myeloma, or human lymphoblastoid lines to yield the immortalized hybridomas. In some instances, it may be desirable to transform a human B-cell producing the desired antibody with an Epstein-Barr virus to produce an immortal cell capable of secreting a human antibody with the desired specificity (see, e.g., U.S. Pat. No. 4,464,465, which is incorporated herein by reference).

The immortalized cell lines may be cloned and screened in accordance with conventional techniques, with the antibodies capable of binding to the epitopes of the markers detected in the cell supernatants. The general fusion, screening, and expansion methods of monoclonal antibody technology are well-known to those skilled in the art and do not form part of the present invention.

Once the antibodies having suitable specificity have been produced, a wide variety of the immunological assay methods may be utilized to ascertain the presence of the markers. Numerous competitive and noncompetitive protein binding assays have been described in the literature, and a large number of such assays are commercially available. Typically, the assays entail the use of labels on the antibodies. A wide variety of labels may be employed, such a radionuclides, fluorescors, enzymes, enzyme substrates, enzyme cofactors, enzyme inhibitors, etc.

Kits can also be supplied for use with the antibodies of the present invention. Thus, the antibodies are typically provided in lyophilized form, either alone or in conjunction with buffers, stabilizers, inert proteins, or the like, in accordance with well-known manufacturing procedures. In a preferred method of the present invention, antibodies will be utilized in immunohistochemical staining procedures for use in detecting the markers in tissue samples. Usually, tissue samples are obtained from surgically-removed tissue which has been frozen and sectioned in sizes from about 5 to 10 microns. The fixed frozen section may be analyzed fixed, such as in formalin, acetone, or other standard histological preservatives, or analyzed unfixed as desired.

The antibodies of the present invention may also find use in whole-body imaging techniques. For example, radioisotope label conjugated to the antibody will permit the location of myoepithelial tumors to be determined.

The antibodies, preferably monoclonal antibodies, reactive with the markers, or binding fragments of the antibodies, are bound to a suitable radioisotope, typically Technetium-99, $^{123}$Iodine, $^{125}$Iodine, $^{131}$Iodine, $^{111}$Indium, or combinations thereof, and administered parenterally. The biodistribution of the label may be monitored by scintigraphy.

Alternatively, the monoclonal antibody, or binding fragment thereof, may be conjugated to cytotoxic drugs to increase specificity of treatment towards target tumor cells. A wide variety of cytotoxic agents are known, such as various radioisotopes, the alkaloid vindesine, the ricin A-chain, daunomycin, and the like. This technique is useful with breast carcinomas that have metastasized and have a necrotic component to which the conjugate can bind and subsequently destroy. Preferred methods of preparing antibody-cytotoxic reagents are well-known to those skilled in the art (e.g., Watanabe et al. (1984) J. Pharm. Dyn. 7:593–603 and Rowland et al., Cancer Immunol. Immunother. (1986) 21:183–187, both of which are incorporated herein by reference).

When used as a component of pharmaceutical compositions, the antibodies are commonly present in conjunction with a pharmaceutically-effective carrier. Amounts effective will vary with the particular utility, but generally range from about 1 to 200 milligrams of antibody per kilogram of body weight, with dosages from 5 to 25 milligrams per kilogram being more commonly used.

The carrier may be any compatible, nontoxic substance suitable for delivery of the antibodies, conjugated or otherwise, to the patient. Sterile water, alcohol, fats, waxes, and inert solids may be included, as well as adjuvants, if desired. The concentration of antibody in these formulations can vary widely, from less than about 0.5% to about 15% or 20% by weight.

Preferably, the pharmaceutical composition will be administered parenterally, that is, subcutaneously, intramuscularly or intravenously. Actual methods for preparing administrable compositions, depending on the mode of administration, are readily available to those skilled in the art and are described in more detail in, for example, *Remington's Pharmaceutical Science* (1980) 15th ed., Mack Publishing Company, Easton, Pa., which is incorporated herein by reference.

The following examples are offered by way of illustration and not limitation.

EXPERIMENTAL

A. Immunization

BALB/c mice raised under pathogen-free conditions were injected via subcutaneous or intravenous routes for 5 weeks at weekly intervals with whole-cell preparations of a secondary culture of an infiltrating ductal breast carcinoma. For each inoculation, $10^6$ cells, which had been cultured as previously described (Smith et al. (1982) *Cancer Chemother. Pharmacol.*, 6:237–244), were prepared by scraping the monolayer with a rubber policeman into phosphate-buffered saline.

B. Monoclonal Antibodies

Splenocytes from immunized animals were fused with SP2/O mouse myeloma cells in the presence of polyethylene glycol ($M_r$4000: Merck) by the procedure of Kohler and Milstein (1975) *Nature (London)*, 256:495–497, which is incorporated herein by reference. Monoclonal antibodies were initially screened by an enzyme-linked immunoassay (EIA), in accordance with well-known procedures. More specifically, the EIA procedure consisted of coating the immunogen onto a solid substrate, incubating it with a test hybridoma supernatant, then incubating with a peroxidase-conjugated goat anti-mouse antibody and thereafter with a peroxidase substrate (4-chloronaphthol) and finally visualizing the antigen-antibody reaction by optical densitometry. The myoepithelium-specific monoclonal antibody designated 312C8-1 (A.T.C.C. Accession No. HB9288) was picked on the basis of its considerably higher optical density with immunogen as compared to skin fibroblasts from the same individual.

C. Immunocytochemical Staining

For immunocytochemical staining of tissue sections, we used fresh surgical specimens of primary breast carcinoma, salivary glands, or skin associated with either normal or malignant mammary gland. These were stored frozen in liquid nitrogen until use. Cryostat sections (thickness, 6 μm) of tissues and pelleted organoids were cut and fixed with acetone before the immunostaining procedure. Primary and secondary human mammary epithelial cultures propagated on coverslips were also fixed with acetone. The reactivity of the monoclonal antibodies was visualized using an avidin-biotin amplification procedure (Vector Laboratories, Calif.). The procedure consisted of an initial blocking step with nonimmune serum, incubation with the monoclonal antibody for 30 minutes at 37° C., incubation with biotin-conjugated antimouse serum (or IgG) for 30 minutes at 37° C., incubation with avidin-biotin-peroxidase conjugate for 30 minutes, and finally precipitation of the colored product using 3,3'-diaminobenzidine. After each incubation, the specimens were counterstained with hematoxylin (and, in some cases, eosin), dehydrated, and mounted in Histomount. Ascites preparations of monoclonal antibodies 312C8-1, 34BE:12, and 43BE8 were used at dilutions of 1:1,000, 1:10,000, and 1:100, respectively. The tissue-culture supernatant of HMFG1 was used undiluted.

In double-immunolabeling studies, coverslip cultures were first incubated with HMFG1, and the reactivity was visualized with gold-conjugated goat antimouse IgG (Boehringer Mannheim. Indianapolis, In.). Photomicrographs were taken, and after several washes with PBS, the same cultures were exposed to monoclonal antibody 312C8-1. The reactivity with this antibody was visualized using the avidin-biotin amplified immunoperoxidase procedure already described.

Generally, reactivity with 312C8-1 was observed without pretreatment of cryostat sections with enzymes or fixatives; however, acetone-fixation of sections mounted on glass slides resulted in improved preservation of the specimens during the immunostaining procedure.

D. Ouchterlony Analysis

Serum-free supernatants were concentrated 10-fold by ammonium sulfate (50%) precipitation, and the class of immunoglobulin present in the concentrate was determined by using commercially available anti-class (IgM) and anti-subclass (IgG1, G2, and G2B) antisera (Miles Laboratories, Inc., Elkhart, Ind.). The 312C8-1 antibody is of the IgM subclass.

E. Preparation of Cytoskeletal Extracts. Frozen blocks of a few specimens that had been analyzed previously by immunocytochemical staining were chosen for the preparation of cytoskeletal extracts. Sections (10 μm thick) were cut from the blocks and extracted by a modification of the procedure of Tseng et al. (1982) Cell 30:361-372. They were first homogenized in 25 mM Tris-HCl (pH 7.4) containing 1 mM phenylmethylsulfonyl fluoride. The resultant suspensions were centrifuged at 10,000×g for 10 minutes at 4° C. The supernatants were discarded, and the residual water-insoluble proteins were then solubilized by heating at 100° C. for 5 minutes in 1% sodium dodecyl sulfate/5% 2-mercaptoethanol/ 25 mM Tris-HCl, pH 7.4, and designated cytoskeletal extracts.

F. Cell Culture

The tissue used in cell cultures was discarded material removed during reduction mammoplasties. The processing of tissue for the separation of epithelial from stromal components was as described in Stampfer et al. (1980) In Vitro, 16:415-425, which is incorporated herein by reference. In brief, minced tissue was digested by gentle rotation at 37° C. in collagenase and hyaluronidase. The enzymatic reaction was terminated when microscopic examination revealed the presence of epithelial clumps (termed "organoids") free of attached stroma. The organoids were collected by filtration with polyester screen filters and then cryopreserved. The organoids were either plated directly onto glass coverslips for immunolocalization studies or were placed in multiple T-25 flasks at 37° C. in a humidified $CO_2$ incubator for more extensive propagation. Epithelium from human milk was obtained by pelleting the cellular components at 1,000 rpm, washing the pellet with phosphate-buffered saline (PBS), and plating the resuspended pellet directly onto glass coverslips. The growth medium used in these studies (MM medium) is an enriched formulation specifically designed for human mammary epithelial cells as described in Stampfer et al., above, Cell lines MCF-7, MDA-231, MDA-468, MDA-549, and MDA-236 were routinely cultured in DME+10% fetal calf serum (FCS).

G. Gel Electrophoresis and Immunoblotting

Cytoskeletal extracts were prepared from cultured cells according to a modified version of the procedure of Franke et al. (1981) Exp. Cell Res., 131:299-318, as follows: monolayers cultured in T75 flasks were washed with cold isotonic saline, scraped with a rubber policeman into 25 mM Tris-HCl (pH 7.4) containing 1 mM phenyl methyl sulfonyl fluoride (PMSF), disrupted in a Dounce homogenizer, and centrifuged at 10,000 g for 10 minutes at 4° C. The supernatants were discarded, and the residual water-insoluble proteins were solubilized by heating at 100° C. for 5 minutes in 1% sodium dodecyl sulfate (SDS) and 5% 2-mercaptoethanol in 25 mM Tris-HCl (pH 7.4) and subsequently used for gel electrophoresis and immunoblotting studies.

One-dimensional SDS-polyacrylamide gel electrophoresis (PAGE) using 10% slab gels was performed according to the method of Laemmli (1970) Nature, 277:680-685. For two-dimensional gel electrophoresis, proteins were separated by nonequilibrium pH gradient electrophoresis (NEPHGE) and then by SDS-PAGE according to the procedure of O'Farrell (1975) J. Biol. Chem., 250:4009-4021. The proteins from unstained polyacrylamide gels were transferred to nitrocellulose paper using the method of Towbin et al. (1979) Proc. Natl. Acad. Sci. USA, 76:4350-4354. To visualize the protein bands and the molecular-weight standards, the blots were stained with Ponceau S for 2 minutes. The molecular-weight standards were marked on the blots using a ball-point pen in order to facilitate the estimation of the apparent molecular weight of the target antigen. The blots were then incubated sequentially through all of the steps already outlined for the avidin-biotin amplified immunocytochemical staining procedure. Incubations were for 1 h at room temperature, and the PBS washes also contained 0.05% Tween 20. The peroxidase substrate used was 4-chloronaphthol. The monoclonal antibody 312C8-1 was typically used at a tenfold higher concentration in the immunoblotting studies.

H. Immunolocalization of Myoepithelium

1. Mammary Gland. Normal breast tissue was derived for this study from two main sources--namely, fresh specimens from reduction mammoplasties or normal tissue peripheral to breast carcinoma. In both cases, the material predominantly consisted of normal mammary ducts and connective tissue. As is generally believed on the basis of ultrastructural studies (Nesland et al. (1983) Diagn. Histopathol., 6:51-67), in normal, mature, nonlactating human mammary ducts, the myoepithelial cells are situated as a continuous layer between the secretory-type epithelial cells and basal lamina. As shown in FIG. 1, the 312C8-1 monoclonal antibody was able to clearly define the myoepithelial cells in the normal human mammary ducts. There was essentially no reactivity with luminal epithelial cells, connective tissue, vasculature, or musculature. This was the general finding in the mature ducts of 13 different specimens. In the case of smaller ducts and ductules in normal breast lobules, the delineation of myoepithelium was not as complete as in the mature ducts shown in FIG. 1.

2. Salivary Glands, Cryostat sections from the parotid and submandibular glands were examined for reactivity with 312C8-1. FIG. 2a indicates that one sample showed a continuous layer of 312C8-1-reactive basal cells, presumably the myoepithelium, in an excretory duct. Luminal epithelium and stromal elements were negative. The reactivity of 312C8-1 with acini showed a discontinuous layer of basal cells (FIG. 2b).

3. Sweat Glands. The human sweat glands are considered to be the most differentiated in comparison to those of other animals. The basic structure of both eccrine and apocrine sweat glands mainly consists of secretory tubules. The walls of the secretory tubules are composed of glandular, secretory cells, and contractile, myoepithelial cells. The glandular cells are comprised of a simple epithelium and are surrounded by the myoepithelial cells (Kurosumi and Ito (1984) Int. Rev. Cytol., 87:253-329). As shown in FIG. 2c, the monoclonal antibody 312C8-1 reacted with only the myoepithelium or the basal cell layer in the sweat glands of skin.

4. Primary Breast Carcinomas. A set of 60 breast carcinoma specimens were studied. The monoclonal antibody 312C8-1 was reactive with several of them in two main distribution patterns. A summary of the patterns of reactivity is presented in Table I. Epithelial cells in all of the specimens were designated as malignant or nonmalignant on the basis of histological appearance. The distribution of reactivity over the tumor population was either homogeneous or heterogeneous, and typically without reactivity with stromal specimens (see, Dairkee et al. (1985) *Proc. Natl. Acad. Sci. USA* 82:7409–7413, which is incorporated herein by reference). Three of 60 tumors were strongly and homogeneously reactive (FIG. 3a). Thirty-five of 60 tumors had either very weak or no visible reactivity at all with the antibody. Twenty-two other tumor specimens were found to be quite heterogeneous in the distribution of the antigen. In several of these specimens, the antibody mainly circled some groups of cells (FIG. 3b). Most often the encircled patches appeared to consist of malignant cells, but it was difficult to ascertain whether some tumor cells in these specimens were exhibiting the antigen or whether the reactivity represented residual myoepithelial cells. In a few specimens, some tumor nests were strongly and homogeneously reactive, while neighboring tumor nests were nonreactive. The reactivity in all malignant specimens also was restricted to tumor cells and all other cell types were nonreactive, e.g., luminal epithelium, stroma, fat, vasculature or musculature from mammary glands.

TABLE I

Immunolocalization of Monoclonal Antibody 312C8-1 in Frozen Sections of Breast Carcinoma Specimens

| Pattern of 312C8-1 Reactivity | Histologic Type | | | | |
|---|---|---|---|---|---|
| | Invasive lobular | Infiltrating ductal | Uncertain (ductal or lobular) | Medullary | Total |
| Strong, homogeneous | 0 | 3 (5%) | 0 | 0 | 3 (5%) |
| Strong, heterogeneous | 0 | 4 (7%) | 0 | 0 | 4 (7%) |
| Circling tumor nests | 1 (2%) | 16 (27%) | 1 (2%) | 0 | 18 (30%) |
| Negative | 8 (13%) | 22 (37%) | 4 (7%) | 1 (2%) | 35 (58%) |

I. Characterization of 312C8-1-Reactive Antigen: NaDod-SO₄/PAGE and Immunoblotting In experiments aimed toward defining the antigen(s) recognized by the 312C8-1 monoclonal antibody, we used cytoskeletal extracts of a strongly and homogeneously reactive breast carcinoma. Cytoskeletal extracts were preferred for this study because the immunoperoxidase localization studies demonstrated a fibrillar array, typical of cytoskeletal proteins. Several polypeptides were visualized by the Coomassie blue dye. However, the results of the immunoblotting experiments indicated a 312C8-1-reactive polypeptide, most probably a keratin, with an apparent molecular weight of 51,000 in the tumor, which was found to be reactive in frozen sections. Tumors that were nonreactive by immunolocalization on frozen tissue were also nonreactive with 312C8-1. We also attempted similar studies on normal breast tissue; not surprisingly, considering the generally low level of the myoepithelial component in comparison to other cell types in the mammary gland, we were unable to detect any 312C8-1-reactive moieties by immunoblotting.

The 51 kd keratin reactive with 312C8-1 is likely a differentiation antigen of the basal epithelial cells of the mammary gland. The protein appears to be keratin 14, or derived from it or a common precursor thereof.

J. Growth and Morphology of Primary and Secondary Mammary-gland Cultures

In this study "primary mammary cultures" refers to the outgrowth of cells obtained after the seeding of organoids onto a solid substrate in MM growth medium. When the primary culture vessel was semiconfluent, the monolayer of cells which had migrated out of the main body of the organoids was lightly trypsinized and transferred to another culture vessel for growth and proliferation, this being referred to as a "secondary mammary culture." Several secondary cultures could be initiated over a period of 2-3 weeks from the original organoid culture. The morphological properties of these cultures have been described in detail by Stampfer et al., cited above. The salient features relevant to the present study are that, in the MM growth medium after the attachment of organoids to the substrate and the initial outgrowth of epithelial cells, there was continuous growth until confluence of cells with a typically polygonal epithelial appearance had been reached. This is in contrast to the findings in basal medium reported by Edwards et al. (1984) *Differentiation* 25:247–258, whose cultures also contained cells with an elongated and fibroblastic morphology. Thus, in both primary and secondary mammary cultures propagated in MM growth medium, an almost pure population of typical polygonal epithelial cells was obtained.

K. Immunoreactivity of Antibodies Against the Luminal and Basal Epithelium Before and After Growth In Culture The 312C8-1 monoclonal antibody was reactive with the basal epithelium in the human mammary gland in vivo. The 34BE12 antibody (see below) reacted with all cells in the mammary epithelial cultures, indicating the absence of fibroblasts. However, these keratinpositive cultured cells could have represented basal or luminal epithelium. The findings demonstrate the expression of both the basal and luminal markers on cells that were morphologically homogeneous.

The reactivity of the antibodies, 34BE12, HMFG1 312C8-1, and 43BE8, with established breast carcinoma cell lines was also examined. The results demonstrated that 34BE12 (against keratin: Gown and Vogel (1984) *Am. J. Pathol.* 114:308–321), 43BE8 (against vimentin; Gown and Vogel, supra), and HMFG1 (against luminal epithelium: Williamson et al. (1984) *Int. J. Cancer.* 33:299–304) were reactive with all cell lines; however, the basal marker, 312C8-1, was consistently nonreactive, indicating that concurrent expression of this marker is not a common occurrence in all cultured mammary epithelial cells. Furthermore, MCF-7 cells (see, Soule et al. (1973) J.N.C.I., 51:1409–1413) cultured in MM medium (i.e., the growth medium used for normal mammary-epithelium culture) or in DME+10% FCS exhibited the same phenotype with respect to the above-mentioned panel of antibodies.

L. Characterization of the 312C8-1-reactive Basal Antigen Expressed in Mammary Cultures Immunochemical characterization of the luminal antigen reactive with the monoclonal antibody, HMFG1, has previously been performed in cultured normal and malignant human mammary epithelial cells. Its reactivity has been shown to be directed against an oligosaccharide determinant in a large glycoprotein component that is also known to be present in the human milk fat globule membrane (Burchell et al. (1983) *J. Immunol.*, 131:508–513).

associated prognosis (e.g., fatality within about two to three years or early recurrence of the breast cancer within about six months to one year post surgical removal of the cancerous tissue).

TABLE II

Relationship of Staining with 312C8-1 Monoclonal Antibody to Other Prognostic Indicators and to Relapse-free Survival Over a 24-month Follow-up (12/86)

| Patent | Date | Age | Tumor Size | Lymph Nodes | ER* | PR** | 312C8-1 Reactivity | Clinical Course |
|---|---|---|---|---|---|---|---|---|
| 1 | 9/83 | 63 | 3 cm | + | − | − | + | Expired 9/85 |
| 2 | 10/84 | 59 | 4 cm | − | − | − | + | Recurrent 7/85 |
| 3 | 10/84 | 70 | 3 cm | − | + | + | + | Recurrent 5/85 |
| 4 | 6/84 | 30 | 5 cm | + | − | − | + | Expired 7/86 |
| 5 | 9/83 | 58 | 7 cm | − | + | + | − | NED*** 9/86 |
| 6 | 1/84 | 54 | 2 cm | + | + | + | − | NED 10/86 |
| 7 | 2/84 | 54 | 2 cm | − | + | + | − | NED 10/86 |
| 8 | 2/84 | 68 | 6 cm | + | + | + | − | NED 10/86 |
| 9 | 4/84 | 50 | 3 cm | n/a | + | + | − | NED 11/85 |
| 10 | 5/84 | 60 | 3 cm | − | − | − | − | NED 9/86 |
| 11 | 8/84 | 76 | 3 cm | − | − | − | − | NED 10/86 |
| 12 | 6/84 | 67 | 2 cm | − | − | − | − | NED 9/86 |
| 13 | 5/84 | 49 | 4 cm | − | − | − | − | NED 6/86 |
| 14 | 5/84 | 38 | 7 cm | − | − | − | − | Expired 12/84 |
| 15 | 3/84 | 31 | 3 cm | + | + | − | − | Recurrent |

*ER = estrogen receptor assay
**PR = progesterone receptor assay
***NED = no evidence of disease assay We attempted to determine whether the reactivity of cultured mammary epithelium indeed represents reactivity of the 312C8-1 antibody with the same polypeptide component as that seen in vivo. Immunoblots with the monoclonal antibody, 312C8-1, on cytoskeletal extracts prepared from secondary cultures of normal mammary epithelium revealed the same 51,000-dalton keratin band at one-dimensional gel electrophoresis. The isoelectric pH of this keratin is 5.4, the same as we have also found in tumor specimens. The keratin reactive with the monoclonal antibody, 312C8-1, is therefore not a unique keratin and is also present in many other organ systems. However, our present results suggest that this keratin is restricted to the basal epithelium in the human mammary gland and is thus a marker specific for human basal epithelium.

M. Prognostication with the 312C8-1 Antibody

Of the mammary carcinomas that were strongly and homogeneously reactive (i.e., at least about 90% expressed the 312C8-1 marker) over essentially the entire tumor cell population (3 of the 60 from Table I and an additional 1 of 40 more subjects), 2 died rapidly from the cancer and 2 suffered a fatal recurrence. Thus, such expression of the epitope reactive with the 312C8-1 antibody is indicative of an aggressive grade of mammary cancer.

A time study of fifteen selected patients (including the four patients from above) inflicted with a mammary carcinoma was conducted. Table II shows a comparison of an assay based on 312C8-1 monoclonal antibody reactivity, as described above, with various standard tumor diagnostic methods is presented, including tumor size, lymph node analysis for malignant cells (see, Fisher et al. (1968) *Am. Surgery* 168:337–356, which is incorporated herein by reference), and estrogen and progesterone receptor biochemical assays (see, Chamness et al. in Thompson and Lippmann, eds., "Steroid Receptors and the Management of Cancer, " CRC Press, U.S.A., 1979, pgs. 3–30). The results of the study showed, unexpectedly, that reactivity of a high proportion of malignant cells with the 312C8-1 monoclonal antibody indicates an aggressive carcinoma with the From the foregoing, it will be appreciated that the use of myoepithelial-specific markers provide reliable methods for the prognosis of aggressive human mammary and other carcinomas, as well as an efficient means for tissue culture analysis of epithelial cell type. The discovery of these markers, in particular, the polypeptide exhibiting the determinant reactive with the 312C8-1 antibody, provides means to develop compositions effective in treating these carcinomas, such as with conjugated antibody preparations.

Although the present invention has been described in some detail by way of illustration and example for purposes of clarity of understanding, it will be obvious that certain changes and modifications may be practiced within the scope of the appended claims.

We claim:

1. A method for determining the prognosis of a malignant carcinoma, said method comprising detecting a marker distribution in a sample of malignant cells from said carcinoma and comparing said distribution with one or more known marker distributions from aggressive or non-aggressive carcinomas, wherein the marker is a basal cell-specific human keratin protein having a molecular weight of about 51,000 daltons and a pI of 5.4, and a homogeneous distribution throughout the sample of malignant cells is indicative of an aggressive grade of carcinoma.

2. A method as in claim 1, wherein the sample is a tissue sample.

3. A method as in claim 2, wherein the tissue sample comprises a frozen section of human mammary tissue.

4. A method as in claim 3, wherein the frozen section of tissue is unfixed.

5. A method as in claim 3, wherein the frozen section is treated with a fixing agent.

6. An immunohistochemical method for identifying an aggressive human mannary carcinoma in a patient, said method comprising the steps of:
   isolating from said patient a tissue specimen suspected of containing cells from said carcinoma;
   incubating a section of the specimen with a monoclonal antibody specifically reactive with a 51,000- dalton cytokeratin protein, wherein the protein exhibits an epitope reactive with the monoclonal antibody 312C8-1 (A.T.C.C. Accession No. HB9288); and determining whether or not the carcinoma is an aggressive carcinoma by detecting the formation of complexes between the antibody and malignant cells, wherein complexes associated with a majority of the malignant cells indicate the presence of said aggressive carcinoma.

7. A method for characterizing subclasses of human epithelial cells in tissue culture, said method comprising reacting said cells with a monoclonal antibody specifically reactive with a marker, wherein the marker is a 51,000-dalton keratin protein having a pI of 5.4 and is specific to basal cells, and then detecting the basal cell-specific marker through immunochemical staining procedures as an indication that the cells bearing the marker are basal epithelial cells.

8. A composition comprising monoclonal antibodies specifically reactive with a human keratin protein exhibiting a molecular weight of about 51,000 daltons and having an isoelectric point of 5.4.

* * * * *